US006409697B2

(12) United States Patent
Eno et al.

(10) Patent No.: US 6,409,697 B2
(45) Date of Patent: Jun. 25, 2002

(54) TRANSMYOCARDIAL IMPLANT WITH FORWARD FLOW BIAS

(75) Inventors: Robert A. Eno, Plymouth; Guy P. Vanney, Blaine, both of MN (US)

(73) Assignee: HeartStent Corporation, St. Paul, MN (US)

( * ) Notice: Subject to any disclaimer, the term of this patent is extended or adjusted under 35 U.S.C. 154(b) by 0 days.

(21) Appl. No.: 09/304,730

(22) Filed: May 4, 1999

(51) Int. Cl.[7] ................. A61M 5/00; A61M 25/00; A61F 2/06; A61B 17/08
(52) U.S. Cl. ................. 604/9; 604/8; 604/264; 623/1.15; 623/11.11; 606/153; 606/194
(58) Field of Search ................. 604/8–10, 264, 604/523; 128/898; 623/1.1, 1.23, 1.3–1.31, 1.36–1.37, 1.44, 1.46, 1.49, 11, 12, 66.1, 902–903, FOR 100

(56) References Cited

U.S. PATENT DOCUMENTS

| 4,546,499 A | * 10/1985 | Possis et al. ................. 623/1 |
| 5,429,144 A | 7/1995 | Wilk |
| 5,655,548 A | 8/1997 | Nelson et al. |
| 5,755,682 A | 5/1998 | Knudson et al. |
| 5,944,019 A | * 8/1999 | Knudson et al. ................. 128/898 |
| 5,984,956 A | * 11/1999 | Tweden et al. ................. 623/1 |
| 6,029,672 A | * 2/2000 | Vanney et al. ................. 128/898 |
| 6,053,942 A | * 4/2000 | Eno et al. ................. 623/1.15 |
| 6,076,529 A | * 6/2000 | Vanney et al. ................. 128/898 |
| 6,113,823 A | * 9/2000 | Eno |
| 6,132,405 A | * 10/2000 | Nilsson et al. |
| 6,182,668 B1 | * 2/2001 | Tweden et al. |

FOREIGN PATENT DOCUMENTS

| WO | WO 98/06356 | 2/1998 |
| WO | WO 98/08456 | * 3/1998 |
| WO | WO 98/46115 | 10/1998 |

* cited by examiner

Primary Examiner—Angela D. Sykes
Assistant Examiner—P Bianco
(74) Attorney, Agent, or Firm—Merchant & Gould P.C.

(57) ABSTRACT

A transmyocardial implant establishes a blood flow path through a heart wall between a heart chamber and a lumen of a coronary vessel on the heart wall. The implant includes a hollow conduit having an open first end and an open second end. The conduit is dimensioned so as to extend at least from the vessel through said heart wall and into said chamber. The conduit has a conduit wall defining a blood flow pathway within an interior of said conduit between the first and second ends. The first and second ends are mutually positioned for the first end to reside within the vessel and opposing a wall of the vessel when the conduit is placed within the heart wall with the second end protruding into the chamber. The conduit wall is formed of a material sufficiently rigid to resist deformation and closure of the pathway in response to contraction of the heart wall. A flow restriction is formed in the pathway for reducing a discharge velocity of blood flow discharged from the first end.

14 Claims, 2 Drawing Sheets

TRANSMYOCARDIAL IMPLANT WITH FORWARD FLOW BIAS

BACKGROUND OF THE INVENTION

1. Field of the Invention

This invention pertains to an implant for passing blood flow directly between a chamber of the heart and a coronary vessel. More particularly, this invention pertains to such an implant with an enhance design for reducing a likelihood of damage to a coronary vessel from a high-velocity blood flow discharge.

2. Description of the Prior Art

Commonly assigned U.S. Pat. No. 5,755,682 and PCT International Publication No. WO 98/06356 teach an implant for defining a blood flow conduit directly from a chamber of the heart to a lumen of a coronary vessel. An embodiment disclosed in the aforementioned patent and application teaches an L-shaped implant. The implant is a conduit having one leg sized to be received within a lumen of a coronary artery and a second leg sized to pass through the myocardium and extend into the left ventricle of the heart. As disclosed in the above-referenced patent and application, the conduit remains open for blood flow to pass through the conduit during both systole and diastole. The conduit penetrates into the left ventricle in order to prevent tissue growth and occlusions over an opening of the conduit.

Commonly assigned and co-pending U.S. patent application Ser. No. 08/944,313 filed Oct. 6, 1997, entitled "Transmyocardial Implant", filed in the name of inventors Katherine S. Tweden, Guy P. Vanney and Thomas L. Odland, issued as U.S. Pat. No. 5,984,956 on Nov. 16, 1999, teaches an implant such as that shown in the aforementioned '682 patent with an enhanced fixation structure. The enhanced fixation structure includes a fabric surrounding at least a portion of the conduit to facilitate tissue growth on the exterior of the implant.

Implants such as those shown in the aforementioned patent and applications include a portion to be placed within a coronary vessel and a portion to be placed within the myocardium. When placing a portion of the implant in the coronary vessel, the vessel is incised a length sufficient to insert the implant. When placed within the coronary vessel, the implant discharges flow axially into the vessel. A portion of an interior surface of the implant portion in the vessel acts as a deflection surface to prevent direct impingement of high velocity blood flow on a vessel wall.

The L-shaped implant described in the foregoing is preferably placed through a surgical procedure (open chest or minimally invasively). The suitability of an implant for minimally invasive or percutaneous procedures is influenced, at least in part, by the external size and shape of the implant. The size can be reduced and shape enhanced by elimination of the vessel portion of the foregoing designs.

SUMMARY OF THE INVENTION

According to a preferred embodiment of the present invention, a transmyocardial implant is disclosed for establishing a blood flow path through a heart wall between a heart chamber and a lumen of a coronary vessel on the heart wall. The implant includes a hollow conduit having an open first end and an open second end. The conduit is dimensioned so as to extend at least from the vessel through said heart wall and into said chamber. The conduit has a conduit wall defining a blood flow pathway within an interior of said conduit between the first and second ends. The first and second ends are mutually positioned for the first end to reside within the vessel and opposing a wall of the vessel when the conduit is placed within the heart wall with the second end protruding into the chamber. The conduit wall is formed of a material sufficiently rigid to resist deformation and closure of the pathway in response to contraction of the heart wall. A flow restriction is formed in the pathway for reducing a discharge velocity of blood flow discharged from the first end.

DESCRIPTION OF THE PREFERRED EMBODIMENT

Figure 1:
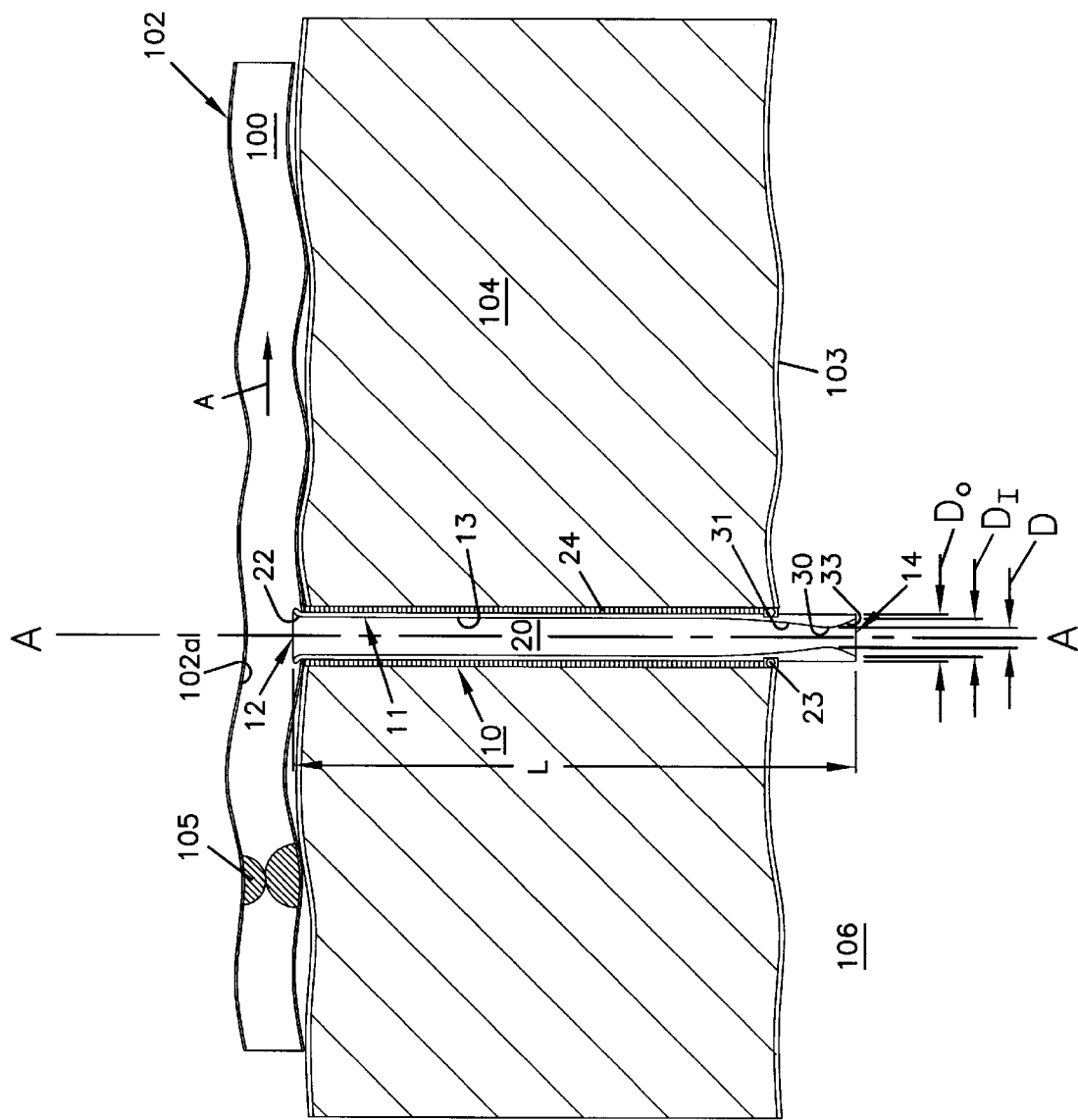
FIG. 1 is a schematic cross-sectional view of an implant according to the present invention in place in a heart wall to define a blood flow path from a left ventricle to a coronary artery distal to an obstruction.

With reference to FIG. 1, an implant 10 is shown including a straight elongate, generally cylindrical tube or conduit 11. The conduit 11 may be formed of titanium or other rigid biocompatible material such as pyrolytic carbon or may be titanium coated with pyrolytic carbon. Preferably, the interior wall 13 of the conduit 11 is polished to a high degree of polish to reduce the likelihood of thrombus formation on the wall. The material of the conduit 11 is preferably a rigid material in order to withstand contraction forces of the heart wall, as will be described.

In the preferred embodiment, the tube 11 will have an outside diameter $D_O$ of about 1 to 3 millimeters and an internal diameter $D_I$ of about 0.5 to 2.5 millimeters to provide a wall thickness of about 0.5 millimeters. By way of non-limiting example, a specific $D_O$ may be 2.5 millimeters and a specific $D_I$ may be 2.0 millimeters.

The size range given permits insertion of the conduit into a coronary vessel to be bypassed. Commonly, such vessels in an adult human have internal diameters of 1 to 3 millimeters when under the influence of normal pressurized blood flow.

The tube 11 has a first open end 12 which is sized to be received within the lumen of a coronary vessel such as the lumen 100 of a coronary artery 102 illustrated in FIG. 1. As used in this application, the term "vessel" refers to veins or arteries. The present invention is described with reference to bypassing a coronary artery with blood from a left ventricle. The invention is equally applicable to forming a blood flow path from other heart chamber to any other coronary vessel.

The conduit 11 has a second open end 14. The conduit 11 is sized to extend from the coronary artery 102 directly through the heart wall 104 and protrude into the left ventricle 106 of a patient's heart. Preferably, the end 14 protrudes at least about 5 millimeters from an inner surface 103 of the heart wall 104 during maximum heart wall thickness during systole. Heart wall thickness varies from patient to patient and among locations on the heart. In a preferred embodiment of forming a flow path from the left ventricle to a coronary artery of an adult human, the length L of the conduit (measured as the axial distance between ends 12 and 14) will be between about 10 and 30 millimeters. With the foregoing specific example, for a heart wall 104 having a maximum systolic thickness of 20 millimeters, the length L of the conduit 11 is 25 millimeters.

The openings 12, 14 communicate with an interior 20 of the conduit 11. Therefore, blood can freely flow through the conduit 11 between the left ventricle 106 and the lumen 100 of the coronary artery 102.

At first opening 12, the conduit 11 is outwardly flared at 22 to act as a stop to limit insertion of the implant 10 into the heart wall 104. Further, the flaring 22 acts as a smooth flow path for guiding blood flow out of end 12.

As mentioned, the tube 11 is preferably formed of titanium or other smooth biocompatible material in order to resist thrombus formation on the inner surface 13 of the conduit 11. Titanium is a presently preferred material due its long-term use in the cardiovascular industry. Further, titanium is sufficiently rigid to withstand deformation forces caused by contraction of the heart wall 104 to avoid deformation of the tube 11 so that the tube 11 remains open during both diastole and systole. Also, the tube 11 is solid on its cylindrical inner surface 13. Therefore, highly thrombogenic material from the heart wall 104 cannot pass into and contaminate the interior 20 of the conduit 11.

While tissue will adhere to titanium, the adhesion may be inadequate when subjected to the shearing contracting forces of the heart wall 104 due to the relative smoothness of extruded titanium. Therefore, a completed implant 10 includes a sleeve 24 of tissue growth-inducing material secured to an exterior surface of the conduit 11. The sleeve 24 is attached to the conduit 11 by a suture 23 tightly surrounding both the sleeve 24 and conduit 11.

The sleeve 24 surrounds the exterior surface of the tube 11 and is recessed back from both of ends 12, 14 so that after placement the sleeve 24 resides solely in the heart wall 104 (although slight protrusion of sleeve 24 into the left ventricle can be tolerated). It is desired the sleeve not be so closely positioned near open ends 12, 14 such that tissue growth on the sleeve 24 can grow over and occlude the open ends 12, 14. It is anticipated that tissue growth on and into the sleeve 24 could result in a buildup of tissue beyond the sleeve 24 to a thickness of about at least 1 millimeter. It is desirable that such tissue growth does not extend over ends 12, 14. Accordingly, the sleeve 24 is spaced from ends of the tube 11 by a distance greater than an anticipated thickness of tissue growth extension beyond the sleeve 24.

The sleeve 24 is selected to induce tissue growth and attachment. Preferably, the sleeve 24 is formed of a fabric having biocompatible fibers defining interstitial spaces to receive tissue growth. An example of such a fabric is polyethylene terephthalate (such as polyester fabric sold by DuPont Company under the trademark DACRON®). Such a fabric permits rapid tissue integration into the fabric thereby anchoring the fabric and, hence, the tube 11 to the patient's tissue.

While a fabric tissue growth inducing material is illustrated, other materials could be used. For example, the tissue growth inducing material could be sintered metal on the external surface of the tube 11. Sintered metal results in a porous surface to receive tissue growth. The area of the sintered metal will be spaced from ends 12, 14 to prevent tissue accumulation on the sintered area from growing over and blocking 12, 14. Alternatively, the exterior surface of the tube 11 can be roughened. The roughening can be in the form of a knurling or other roughened surface due to sandblasting or the application of sinter beads. The roughening results in surface protrusions and pitting, around which tissue may grow.

The implant 10 is placed with the first end 12 placed within the artery lumen 100 distal to an obstruction 105. Normal nourishing blood flow is in the direction of arrow A. The implant 10 passes through the heart wall 104 with the second end 14 positioned within the left ventricle 106 and spaced from the inner surface 103 of the heart wall 104 by 5 millimeters during periods of maximum heart wall thickness. The sleeve 24 is positioned opposing the heart wall 104 so that tissue from the heart wall 104 can grow into the sleeve 24.

With the positioning thus described, the first opening 12 opposes a wall 102a of the artery 102. As a result, blood discharged from the opening 12 impinges directly upon the arterial wall 102a.

The artery wall 102a is a fragile layer of cells and fibers. Direct impingement of blood flow on the wall 102a can damage the artery wall 102a. As a healing response to such damage, a cellular matrix may develop and proliferate to such an extent that opening 12 or lumen 100 could occlude.

The present invention reduces the velocity of blood flow through the opening 12. Specifically, a flow restriction in the form of a narrowing 30 is placed within the conduit 11. The restriction 30 reduces blood flow below a velocity which would otherwise cause occluding trauma to the artery wall 102a.

Figure 1A:
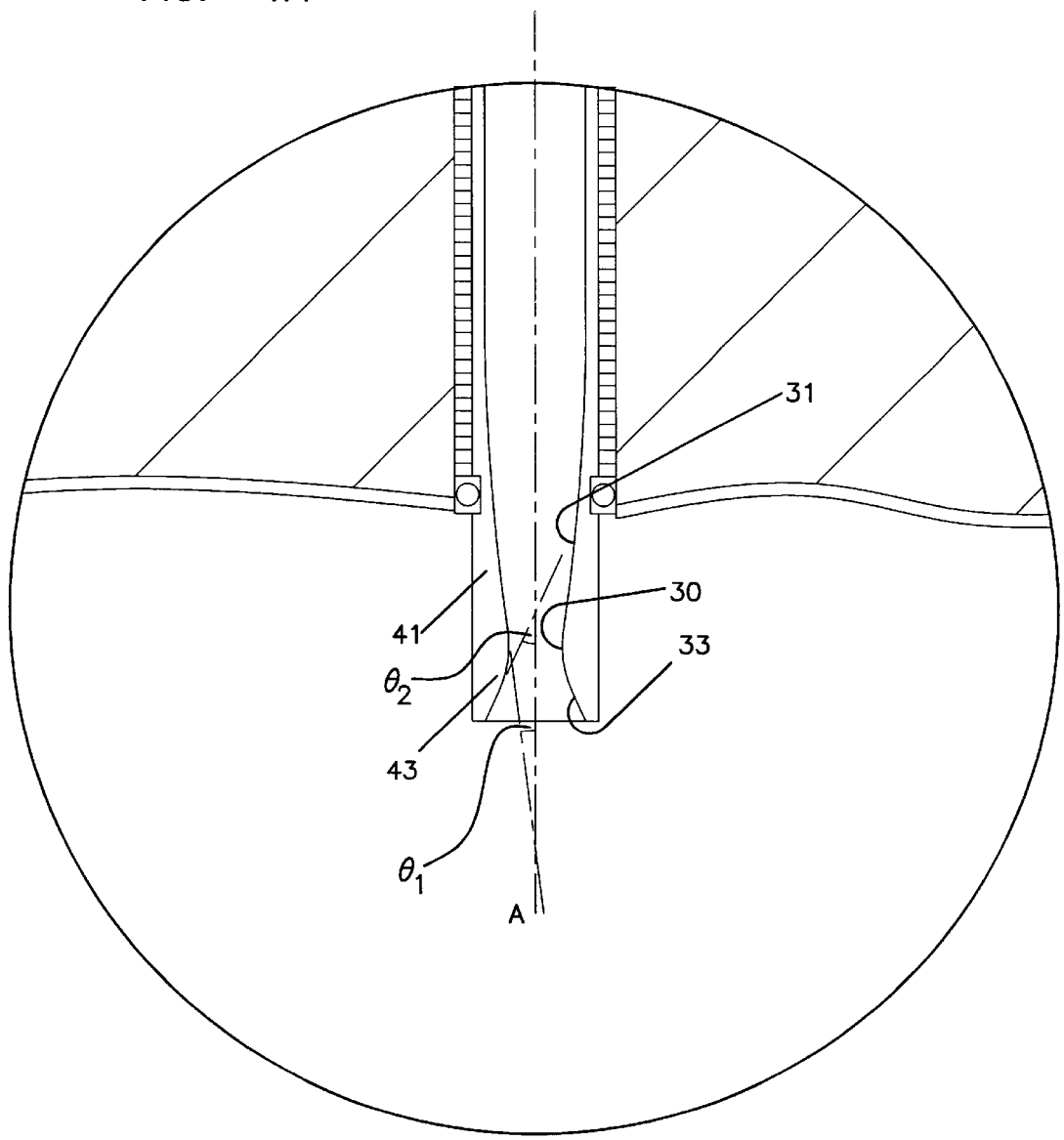
FIG. 1A is an enlarged, schematic cross-sectional view of a portion of the implant of FIG. 1.

With the specific example given, the restriction 30 results in a narrow interior diameter D of about 0.5 millimeters. The narrow restriction 30 is positioned about 8 millimeters from end 14. The restriction 30 is formed by a venturi constriction formed within the conduit 11 adjacent end 14. The venturi may be formed by machining the conduit 11 from a solid blank of titanium. The venturi 30 has a shallow ramp 31 on a downstream side to avoid turbulence. Since an upstream side 33 is adjacent end 14, turbulence during reverse flow is not a serious concern. The shallow ramp 31 on the downstream side of the restriction 30 defines a first inner diameter transition 41 extending from the restriction 30 towards the first end 12. The upstream side 33 of the conduit 11 defines a second inner diameter transition 43 extending from the restriction 30 towards the second end 14. As shown in FIG. 1A, the first inner diameter transition 41 defines a first angle of transition $\theta_1$ with respect to a central axis A—A (FIG. 1) through the center of the conduit 11. Similarly, the second inner diameter transition 43 defines a second angle of transition $\theta_2$ with respect to the central axis A—A. The first angle of transition $\theta_1$ is depicted as being smaller than the second angle of transition $\theta_2$. Accordingly, the second inner diameter transition 43 is steeper than the first inner diameter transition 41. Similarly, as shown in FIG. 1A, the length of the first inner diameter transition is longer than the length of the second inner diameter transition.

With the restriction 30 as described, flow velocity out of end 12 is reduced below a level which would otherwise cause occluding trauma to the artery wall 102a. By avoiding such trauma, a straight implant 10 can be provided which is more susceptible to minimally invasive and percutaneous implantation as well as being suitable for traditional surgical approaches.

Preferably, the blood flow velocity from end 12 is reduced to a velocity of normal blood flow within an artery 102 (about 30 ml/min.). Since the left ventricle 106 has a high maximum pressure, the pressure differential between the ventricle 106 and artery lumen 100 results in a higher than normal blood flow rate in the absence of the restriction 30.

Having disclosed the present invention in a preferred embodiment, it will be appreciated that modifications and equivalents may occur to one of ordinary skill in the art having the benefits of the teachings of the present invention. It is intended that such modifications shall be included within the scope of the claims appended hereto. For example, in the preferred embodiment shown, the tube 11 is a cylinder with circular cross-section. The tube 11 could have an oval cross-section at end 12 to provide a larger flow area and further reduce flow velocity. Also, while the tube 11 is preferably straight, the tube 11 could be bent so that the direction of blood flow from end 12 is not perpendicular to the arterial blood flow direction A.

What is claimed:

1. A transmyocardial implant for establishing a blood flow path through a heart wall between a heart chamber and a lumen of a coronary vessel at said heart wall, said implant comprising:

a hollow conduit having an open first end and an open second end, said conduit sized to extend at least from said vessel through said heart wall and to said chamber, said conduit having a conduit wall defining a blood flow pathway within an interior of said conduit between said first and second ends;

said first and second ends mutually positioned for said first end to reside within said vessel and unobstructively opposing a wall of said vessel when said conduit is placed within said heart wall with said second end positioned at said chamber;

said conduit wall formed of a material sufficiently rigid to resist deformation and closure of said pathway in response to contraction of said heart wall;

a flow restriction formed in said pathway for reducing a discharge velocity of blood flow discharged from said first end, said flow restriction including a permanent, non-varying narrowing of said conduit within said pathway and between said first and second ends to define a permanent, non-varying restricted flow region spaced at an intermediate location between said first and second ends; and the conduit wall defining a first inner diameter transition extending from a region of maximum restriction towards said first end and a second inner diameter transition extending from said region of maximum restriction towards said second end; said first inner diameter transition defining a smaller angle of transition relative to a central reference axis than said second inner diameter transition.

2. A transmyocardial implant according to claim 1 further comprising a tissue growth inducing material surrounding said conduit wall.

3. A transmyocardial implant according to claim 2 wherein said tissue growth inducing material includes a plurality of fibers defining a plurality of interstitial spaces for receiving tissue growth and said tissue growth inducing material is biocompatible.

4. A transmyocardial implant according to claim 3 wherein said tissue growth inducing material is a polyester fabric.

5. A transmyocardial implant according to claim 2 wherein said tissue growth inducing material include a porous layer on said exterior of said conduit.

6. A transmyocardial implant according to claim 5 wherein said tissue growth inducing material includes a sintered layer.

7. A transmyocardial implant according to claim 2 wherein an external area of said conduit surrounded by said tissue growth inducing material is abraded.

8. A transmyocardial implant according to claim 1 wherein said restriction is a narrowing in said pathway positioned between enlarged cross-sectional areas of said pathway.

9. A transmyocardial implant according to claim 8 wherein said pathway has a substantially straight longitudinal axis between said first and second ends.

10. A transmyocardial implant according to claim 1 wherein said flow restriction is selected for said discharge velocity to be less than an occluding trauma inducing velocity.

11. A transmyocardial implant according to claim 1 wherein said conduit is sized for said second end to extend into said chamber beyond said heart wall.

12. A transmyocardial implant according to claim 1 wherein said first inner diameter transition is longer than said second inner diameter transition.

13. A transmyocardial implant according to claim 1 wherein said flow restriction is formed in said pathway adjacent to said second end.

14. A method for establishing a blood flow path through a heart wall between a heart chamber and a lumen of a coronary vessel at said heart wall, said method comprising:

forming a blood flow pathway from said vessel through said heart wall and into said chamber;

maintaining said blood flow path open during both systole and diastole;

restricting blood flow through said pathway to reduce a discharge velocity of blood flow discharged into said vessel, by permanently restricting flow through said pathway at a restriction point within said pathway and spaced from and between first and second ends of said pathway and with said restriction being permanent and non-varying; said first end being positioned adjacent said vessel and said second end being positioned adjacent said heart chamber; said pathway defining a first inner diameter transition extending from a region of maximum restriction towards said first end and a second inner diameter transition extending from said region of maximum restriction towards said second end; said first inner diameter transition defining a smaller angle of transition relative to a central reference axis than said second inner diameter transition.

* * * * *